US008075909B2

(12) United States Patent
Chauhan et al.

(10) Patent No.: US 8,075,909 B2
(45) Date of Patent: Dec. 13, 2011

(54) CONTACT LENS BASED BIOACTIVE AGENT DELIVERY SYSTEM

(75) Inventors: Anuj Chauhan, Gainesville, FL (US); Yash Kapoor, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1132 days.

(21) Appl. No.: 11/896,608

(22) Filed: Sep. 4, 2007

(65) Prior Publication Data
US 2009/0060981 A1 Mar. 5, 2009

(51) Int. Cl.
*A61K 9/113* (2006.01)

(52) U.S. Cl. .................................................... 424/429

(58) Field of Classification Search .................. None
See application file for complete search history.

(56) References Cited

U.S. PATENT DOCUMENTS

| 5,034,461 A | 7/1991 | Lai et al. |
| 5,410,016 A | 4/1995 | Hubbell et al. |
| 5,412,072 A | 5/1995 | Sakarai et al. |
| 5,449,513 A | 9/1995 | Yokoyama et al. |
| 5,496,871 A | 3/1996 | Lai et al. |
| 5,610,252 A | 3/1997 | Bambury et al. |
| 5,693,751 A | 12/1997 | Sakurai et al. |
| 5,723,131 A | 3/1998 | Schultz et al. |
| 5,925,720 A | 7/1999 | Kataoka et al. |
| 5,929,177 A | 7/1999 | Kataoka et al. |
| 6,410,045 B1 | 6/2002 | Schultz |
| 7,037,517 B2 | 5/2006 | Kataoka et al. |
| 7,674,478 B2 | 3/2010 | Kataoka et al. |
| 2004/0120982 A1 | 6/2004 | Diana et al. |
| 2004/0241207 A1 | 12/2004 | Chauhan et al. |
| 2006/0177483 A1 | 8/2006 | Byrne et al. |
| 2006/0246113 A1 | 11/2006 | Griffith et al. |

FOREIGN PATENT DOCUMENTS

| WO | WO 96/32434 | 10/1996 |
| WO | WO 96/33233 | 10/1996 |
| WO | WO 97/00623 | 1/1997 |

OTHER PUBLICATIONS

International Search Report dated Apr. 21, 2009 in corresponding application PCT/US2008/010353.
Written Opinion of the International Searching Authority in corresponding application PCT/US2008/010353 dated Apr. 21, 2009.
Rodriguez R, Alvarez-Lorenzo C, Concheiro A, "Influence of cationic cellulose structure on its interactions with sodium dodecylsulfate: implications on the properties of the aqueous dispersions and hydrogels", European Journal of Pharmaceutics and Biopharmaceutics 56 (1): 133-142 2003.
Barreiro-Iglesias R, Alvarez-Lorenzo C, Concheiro A, "Thermal and FTIR characterization of films obtained from carbopol/surfactant aqueous solutions", Journal of Thermal Analysis and Calorimetry, 68 (2): 479-488 2002, 2005.

(Continued)

*Primary Examiner* — Carlos Azpuru
(74) *Attorney, Agent, or Firm* — Miles & Stockbridge P.C.; David R. Schafter, Esq.

(57) ABSTRACT

A bioactive agent delivery system comprising an optically transparent contact lens having dispersed therein (1) an ophthalmically bioactive agent capable of diffusion through the contact lens and into the post-lens tear film when placed on the eye and (2) associated with the bioactive agent, an ophthalmically compatible polymeric surfactant in an amount sufficient to slow the rate of migration of the bioactive agent through the contact lens.

15 Claims, 4 Drawing Sheets

OTHER PUBLICATIONS

Barreiro-Iglesias R, Alvarez-Lorenzo C, Concheiro A, "Incorporation of small quantities of surfactants as a way to improve the rheological and diffusional behavior of carbopol gels", Journal of Controlled Release, 77 (1-2): 59-75, 2001.

Paulsson M, Edsman K, "Controlled drug release from gels using lipophilic interactions of charged substances with surfactants and polymers", Journal of Colloid and Interface Science, 248 (1): 194-200, 2002.

Paulsson M, Edsman K, "Controlled drug release from gels using surfactant aggregates. II. Vesicles formed from mixtures of amphiphilic drugs and oppositely charged surfactants", Pharmaceutical Research, 18 (11): 1586-1592, 2001, Colloids and Surfaces B-Biointerfaces, 46 (3): 142-146.

Paulsson M, Edsman K, "Controlled drug release from gels using surfactant aggregates: I. Effect of lipophilic interactions for a series of uncharged substances", Journal of Pharmaceutical Sciences, 90 (9): 1216-1225, 2001.

Mandell, R.B., "*Contact Lens Practice: Hard and Flexible Lenses*", 2nd ed., Charles C. Thomas, Springfield, vol. 3, 1974.

Creech, J.L., Chauhan, A., Radke, C.J., "*Dispersive mixing in the posterior tear film under a soft contact lens*", I&EC Research, 2001, 40: 3015-3026.

McNamara, N.A., Polse, K.A., Brand, R.D., Graham, A.D., Chan, J.S., McKenney, C.D., "*Tear mixing under a soft contact lens: Effects of lens diameter*". Am. J. of Ophth., 1999, 127(6): 659-65].

Nagarsenker, M.S., Londhe, V.Y., Nadkarni, G.D., "*Preparation and evaluation of liposomal formulations of tropicamide for ocular delivery*", Int. J. of Pharm., 1990, 190: 63-71.

Lang, J.C., "*Ocular drug delivery conventional ocular formulations*". Adv. Drug Delivery, 1995, 16: 39-43.

Bourlais, C.L., Acar, L., Zia H., Sado, P.A., Needham, T., Leverge, R., "*Ophthalmic drug delivery systems*", Progress in retinal and eye research, 1998, 17, 1: 33-58.

Segal, M., "*Patches, pumps and timed release*", FDA Consumer magazine, Oct. 1991.

Hehl, E.M., Beck, R., Luthard K., Guthoff R., "*Improved penetration of aminoglycosides and fluoroquinolones into the aqueous humour of patients by means of Acuvue contact lenses*", European Journal of Clinical Pharmacology, 1999, 55 (4): 317-323.

Hillman, J. S., "Management of acute glaucoma with Pilocarpine-soaked hydrophilic lens" Brit. J. Ophthal.58 (1974) p. 674-679.

Ramer, R. and Gasset, A., "Ocular Penetration of Pilocarpine:" Ann. Ophthalmol.6, (1974) p. 1325-1327.

Montague, R. and Wakins, R., "Pilocarpine dispensation for the soft hydrophilic contact lens" Brit .J. Ophthal. 59, (1975) p. 455-458.

Hillman, J.,Masters, J. and Broad, A. "Pilocarpine delivery by hydrophilic lens in the management of acute glaucoma" Trans. Ophthal. Soc.U. K. (1975) p. 79-84.

Giambattista, B.,Virno, M., Pecori-Giraldi, Pellegrino, N. and Motolese, E. "Possibility of Isoproterenol Therapy with Soft Contact Lenses: Ocular Hypotension Without Systemic Effects" Ann. Ophthalmol 8 (1976) p. 819-829.

Marmion, V. J. and Yardakul, S. "Pilocarpine administration by contact lens" Trans. Ophthal. Soc.U. K. 97, (1977) p. 162-163.

Hiratani H, Alvarez-Lorenzo C—"The nature of backbone monomers determines the performance of imprinted soft contact lenses as timolol drug delivery systems" Biomaterials 25,1105-1113, 2004.

Hiratani H, Fujiwara A, Tamiya Y, Mizutani Y, Alvarez-Lorenzo C—"Ocular release of timolol from molecularly imprinted soft contact lenses" Biomaterials 26,1293-1298, 2005.

Hiratani H, Mizutani Y, Alvarez-Lorenzo C—"Controlling drug release from imprinted hydrogels by modifying the characteristics of the imprinted cavities" Macromol Biosci 5,728-733, 2005.

Alverez-Lorenzo C, Hiratani H, Gomez-Amoza JL, Martinez-Pacheco R, Souto C, Concheiro A—"Soft contact lenses capable of sustained delivery of timolol" J Pharm Sci 91,2182-2192, 2002.

Hiratani H, Alvarez-Lorenzo C—"Timolol uptake and release by imprinted soft contact lenses made of N,N-diethylacrylamide and methacrylic acid" J Control Release 83,223-230, 2002].

Elisseeff, J., McIntosh, W., Anseth, K., Riley, S., Ragan, P., Langer, R., "*Photoencapsulation of chondrocytes in poly(ethylene oxide)-based semi-interpenetrating networks*", Journal of Biomedical Materials Research, 2000, 51 (2): 164-171.

Ward, J. H., Peppas, N. A., "*Preparation of controlled release systems by free-radical UV polymerizations in the presence of a drug*", Journal of Controlled Release, 2001, 71 (2): 183-192.

Scott, R. A., Peppas, N. A., "*Highly crosslinked, PEG-containing copolymers for sustained solute delivery*", Biomaterials, 1999, 20 (15): 1371-1380.

Podual, K., Doyle F. J., Peppas N. A., "*Preparation and dynamic response of cationic copolymer hydrogels containing glucose oxidase*", Polymer, 2000, 41 (11): 3975-3983.

Colombo, P., Bettini, R., Peppas, N.A., "*Observation of swelling process and diffusion front position during swelling in hydroxypropyl methyl cellulose (HPMC) matrices containing a soluble drug*", Journal of Controlled Release, 1999, 61 (1,2): 83-91.

Ende, M.T.A., Peppas, N.A., "*Transport of ionizable drugs and proteins in crosslinked poly(acrylic acid) and poly(acrylic acid-co-2-hydroxyethyl methacrylate) hydrogels. 2. Diffusion and release studies* ", Journal of Controlled Release, 1997, 48 (1): 47-56.

Gulsen D, Chauhan A—"Dispersion of microemulsion drops in HEMA hydrogel: a potential ophthalmic drug delivery vehicle". Int J Pharm 292,95-117, 2005.

Gulsen D, Chauhan A—"Ophthalmic drug delivery through contact lenses". Invest Ophth Vis Sci 45,2342-2347, 2004.

Graziacascone, M., Zhu, Z., Borselli, F., Lazzeri, L., "Poly(vinyl alcohol) hydrogels as hydrophilic matrices for the release of lipophilic drugs loaded in PLGA nanoparticles", Journal of Material Science: Materials in Medicine, 2002, 13: 29-32].

Rodriguez R, Alvarez-Lorenzo C, Concheiro A, "Interactions of ibuprofen with cationic polysaccharides in aqueous dispersions and hydrogels rheological and diffusional implications", European Journal of Pharmaceutical Sciences 20 (4-5): 429-438, 2003.

Rodriguez R, Alvarez-Lorenzo C, Concheiro A, "Influence of cationic cellulose structure on its interactions with sodium dodecylsulfate: implications on the properties of the aqueous dispersions and hydrogels", European Journal of Pharmaceutics and Biopharmaceutics 56 (1): 133-142 2003.

Barreiro-Iglesias R, Alvarez-Lorenzo C, Concheiro A, "Thermal and FTIR characterization of films obtained from carbopol/surfactant aqueous solutions", Journal of Thermal Analysis and Calorimetry, 68 (2): 479-488 2002, 2005.

Barreiro-Iglesias R, Alvarez-Lorenzo C, Concheiro A, "Incorporation of small quantities of surfactants as a way to improve the rheological and diffusional behavior of carbopol gels", Journal of Controlled Release, 77 (1-2): 59-75, 2001.

Paulsson M, Edsman K, "Controlled drug release from gels using lipophilic interactions of charged substances with surfactants and polymers", Journal of Colloid and Interface Science, 248 (1): 194-200, 2002.

Paulsson M, Edsman K, "Controlled drug release from gels using surfactant aggregates. II. Vesicles formed from mixtures of amphiphilic drugs and oppositely charged surfactants", Pharmaceutical Research, 18 (11): 1586-1592, 2001, Colloids and Surfaces B-Biointerfaces, 46 (3): 142-146.

Paulsson M, Edsman K, "Controlled drug release from gels using surfactant aggregates: I. Effect of lipophilic interactions for a series of uncharged substances", Journal of Pharmaceutical Sciences, 90 (9): 1216-1225, 2001.

Mandell, R.B., "*Contact Lens Practice: Hard and Flexible Lenses*", 2nd ed., Charles C. Thomas, Springfield, vol. 3, 1974.

Bourlais, C.L., Acar, L., Zia H., Sado, P.A., Needham, T., Leverge, R., "*Ophthalmic drug delivery systems*", Progress in retinal and eye research, 1998, 17, 1: 33-58.

Creech, J.L., Chauhan, A., Radke, C.J., "*Dispersive mixing in the posterior tear film under a soft contact lens*", I&EC Research, 2001, 40: 3015-3026.

McNamara, N.A., Polse, K.A., Brand, R.D., Graham, A.D., Chan, J.S., McKenney, C.D., "*Tear mixing under a soft contact lens: Effects of lens diameter*". Am. J. of Ophth., 1999, 127(6): 659-65].

CONTACT LENS BASED BIOACTIVE AGENT DELIVERY SYSTEM

BACKGROUND OF THE INVENTION

1. Field of the Invention

The present invention relates to methods and systems for the delivery of ophthalmic drugs and other bioactive agents to the eye.

2. Description of the Prior Art

Providing and maintaining adequate concentrations of bioactive agents, such as drugs, for example, in the pre-corneal tear film for extended periods of time is one of the major problems plaguing methods and systems for ocular drug delivery. When they are applied as eye drops, most drugs penetrate poorly through the cornea. Drainage of instilled drug with the tear fluid, and absorption through the conjunctiva leads to a short duration of action. The additional pre-corneal factors that contribute to the poor ocular bio-availability of many drugs when instilled in the eye as drops are tear turnover and drug binding to tear fluid proteins. In addition to the above factors, the rate of corneal uptake is high at early times, but it declines rapidly. This may lead to a transient period of overdose and associated risk of side effects followed by an extended period of sub-therapeutic levels before the administration of next dose. All the above factors indicate the need for an ocular drug delivery system that will be as convenient as a drop but will serve as a controlled release vehicle [Nagarsenker, M. S., Londhe, V. Y., Nadkarni, G. D., "*Preparation and evaluation of liposomal formulations of tropicamide for ocular delivery*", Int. J. of Pharm., 1990, 190: 63-71].

Topical delivery via eye drops that accounts for about 90% of all ophthalmic formulations is very inefficient and in some instances leads to serious side effects [Lang, J. C., "*Ocular drug delivery conventional ocular formulations*". Adv. Drug Delivery, 1995, 16: 39-43]. Only about 5% of the drug applied as drops penetrate through the cornea and reaches the ocular tissue, while the rest is lost due to tear drainage [Bourlais, C. L., Acar, L., Zia H., Sado, P. A., Needham, T., Leverge, R., "*Ophthalmic drug delivery systems*", Progress in retinal and eye research, 1998, 17, 1: 33-58]. The drug mixes with the fluid present in the tear film upon instillation and has a short residence time of about 2-5 minutes in the film. About 5% of the drug gets absorbed and the remaining flows through the upper and the lower canaliculi into the lacrimal sac. The drug containing tear fluid is carried from the lacrimal sac into the nasolacrimal duct, and eventually, the drug gets absorbed into the bloodstream. This absorption leads to drug wastage and more importantly, the presence of certain drugs in the bloodstream leads to undesirable side effects. For example, beta-blockers such as Timolol that is used in the treatment of wide-angle glaucoma have a deleterious effect on heart [TIMPOTIC® prescribing information, supplied by MERCK]. Furthermore, application of ophthalmic drugs as drops results in a rapid variation in drug delivery rates to the cornea that limits the efficacy of therapeutic systems [Segal, M., "*Patches, pumps and timed release*", FDA *Consumer* magazine, October 1991]. Thus, there is a need for new ophthalmic drug delivery systems that increase the residence time of the drug in the eye, thereby reducing wastage and eliminating side effects.

There have been a number of attempts in the past to use contact lenses for ophthalmic drug delivery; however, all of these focused on soaking the lens in drug solution followed by insertion into the eye. In one of the studies, the authors focused on soaking the lens in eye-drop solutions for one hour followed by lens insertion in the eye [Hehl, E. M., Beck, R., Luthard K., Guthoff R., "*Improved penetration of aminoglycosides and fluoroquinolones into the aqueous humour of patients by means of Acuvue contact lenses*", European Journal of Clinical Pharmacology, 1999, 55 (4): 317-323]. Five different drugs were studied and it was concluded that the amount of drug released by the lenses are lower or of the same order of magnitude as the drug released by eye drops. This happened perhaps because the maximum drug concentration obtained in the lens matrix is limited to the equilibrium concentration. In another study researchers developed a contact lens with a hollow cavity by bonding together two separate pieces of lens material [Nakada, K., Sugiyama, A., "*Process for producing controlled drug-release contact lens, and controlled drug-release contact lens thereby produced*"; U.S. Pat. No. 6,027,745, May 29, 1998]. The compound lens is soaked in the drug solution. The lens imbibes the drug solution and slowly releases it upon insertion in the eye. The compound lens suffers from the same limitations as the drug-soaked lens because the concentration of the drug in the cavity is the same as the concentration of the drug in the drops and thus such a lens can supply the drug for a limited amount of time. Furthermore, the presence of two separate sheets of lens material leads to smaller oxygen and carbon dioxide permeabilities that can cause an edema in the corneal tissue. The other studies and patents listed below suffer from the same limitations because they are also based on soaking of contact lenses or similar devices in drug-solutions followed by insertion into the eye [Hillman, J. S., "Management of acute glaucoma with Pilocarpine-soaked hydrophilic lens" Brit. J. Ophthal. 58 (1974) p. 674-679, Ramer, R. and Gasset, A., "Ocular Penetration of Pilocarpine:" Ann. Opthalmol. 6, (1974) p. 1325-1327, Montague, R. and Wakins, R., "Pilocarpine dispensation for the soft hydrophilic contact lens" Brit. J. Ophthal. 59, (1975) p. 455-458, Hillman, J., Masters, J. and Broad, A. "Pilocarpine delivery by hydrophilic lens in the management of acute glaucoma" Trans. Ophthal. Soc. U. K. (1975) p. 79-84, Giambattista, B., Virno, M., Pecori-Giraldi, Pellegrino, N. and Motolese, E. "Possibility of Isoproterenol Therapy with Soft Contact Lenses: Ocular Hypotension Without Systemic Effects" Ann. Opthalmol 8 (1976) p. 819-829, Marmion, V. J. and Yardakul, S. "Pilocarpine administration by contact lens" Trans. Ophthal. Soc. U. K. 97, (1977) p. 162-3, U.S. Pat. No. 6,410,045, Drug delivery system for antiglaucomatous medication, Schultz; Clyde Lewis, Mint; Janet M; U.S. Pat. No. 4,484,922, Occular device, Rosenwald; Peter L., U.S. Pat. No. 5,723,131, Contact lens containing a leachable absorbed material, Schultz; Clyde L. Nunez; Ivan M.; Silor; David L.; Neil; Michele L.].

A number of researchers have focused on developing 'imprinted' contact lenses [Hiratani H, Alvarez-Lorenzo C— "The nature of backbone monomers determines the performance of imprinted soft contact lenses as timolol drug delivery systems" Biomaterials 25, 1105-1113, 2004; Hiratani H, Fujiwara A, Tamiya Y, Mizutani Y, Alvarez-Lorenzo C— "Ocular release of timolol from molecularly imprinted soft contact lenses" Biomaterials 26, 1293-1298, 2005; Hiratani H, Mizutani Y, Alvarez-Lorenzo C-"Controlling drug release from imprinted hydrogels by modifying the characteristics of the imprinted cavities" Macromol Biosci 5,728-733, 2005: Alvarez-Lorenzo C, Hiratani H, Gomez-Amoza J L, Martinez-Pacheco R, Souto C, Concheiro A—"Soft contact lenses capable of sustained delivery of timolol" J Pharm Sci 91, 2182-2192, 2002; Hiratani H, Alvarez-Lorenzo C—"Timolol uptake and release by imprinted soft contact lenses made of N,N-diethylacrylamide and methacrylic acid" J Control Release 83,223-230, 2002]. The imprinting leads to an increase in the partition coefficients and slower release of drugs, but the increase is not very substantial, and these lenses typically have an initial burst release.

A number of researchers have trapped proteins, cells and drugs in hydrogel matrices by polymerizing the monomers that comprise the hydrogel, in presence of the encapsulated species [Elisseeff, J., McIntosh, W., Anseth, K., Riley, S., Ragan, P., Langer, R., "*Photoencapsulation of chondrocytes in poly(ethylene oxide)-based semi-interpenetrating networks*", Journal of Biomedical Materials Research, 2000, 51 (2): 164-171; Ward, J. H., Peppas, N. A., "*Preparation of controlled release systems by free-radical UV polymerizations in the presence of a drug*", Journal of Controlled Release, 2001, 71 (2): 183-192; Scott, R. A., Peppas, N. A., "Highly crosslinked, *PEG-containing copolymers for sustained solute delivery*", Biomaterials, 1999, 20 (15): 1371-1380; Podual, K., Doyle F. J., Peppas N. A., "*Preparation and dynamic response of cationic copolymer hydrogels containing glucose oxidase*", Polymer, 2000, 41 (11): 3975-3983; Colombo, P., Bettini, R., Peppas, N. A., "*Observation of swelling process and diffusion front position during swelling in hydroxypropyl methyl cellulose (HPMC) matrices containing a soluble drug*", Journal of Controlled Release, 1999, 61 (1,2): 83-91; Ende, M. T. A., Peppas, N. A., "*Transport of ionizable drugs and proteins in crosslinked poly(acrylic acid) and poly(acrylic acid-co-2-hydroxyethyl methacrylate) hydrogels. 2. Diffusion and release studies*", Journal of Controlled Release, 1997, 48 (1): 47-56; U.S. Pat. No. 4,668,506]. Although direct entrapment of drug could lead to higher loading, in a majority of cases, the loaded drug is released rapidly from contact lenses.

Recently, it has been suggested to disperse in contact lenses nanoparticles of ophthalmic bioactive agents nanoencapsulated in a material from which the ophthalmic drug is capable of diffusion into and migration through the contact lens and into the post-lens tear film when the contact lens is placed on the eye [Gulsen D, Chauhan A—"Dispersion of microemulsion drops in HEMA hydrogel: a potential ophthalmic drug delivery vehicle". Int J Pharm 292, 95-117, 2005., Gulsen D, Chauhan A—"Ophthalmic drug delivery through contact lenses". Invest Ophth V is Sci 45, 2342-2347, 2004.] Also Graziacascone et al. discloses a study on encapsulating lipophilic drugs inside nanopallicles, and entrapping the particles in hydrogels. [Graziacascone, M., Zhu, Z., Borselli, F., Lazzeri, L., "Poly(vinyl alcohol) hydrogels as hydrophilic matrices for the release of lipophilic drugs loaded in PLGA nanoparticles", Journal of Material Science: Materials in Medicine, 2002, 13: 29-32]. They used PVA hydrogels as hydrophilic matrices for the release of lipophilic drugs loaded in PLGA particles. These systems are potentially useful but display the shortcoming of burst release due to the presence of the drug outside the particles. Also, these systems required formulations of nanoparticles followed by addition of these nanoparticles to the polymerizing medium. The solution is then required to be polymerized to trap the nanoparticles in the gel. Thus this is a multistep procedure for making nanoparticle-laden contact lenses, which is not optimal. Furthermore, there is a possibility that some nanoparticles may degrade during the gel polymerization step.

The present invention seeks to overcome these obstacles utilizing surfactants to slow down the release rates of drugs from contact lenses. The use of surfactants to retard drug release rates from polymeric gels has been reported but none of these focused on creating surfactant-laden contact lenses [Rodriguez R, Alvarez-Lorenzo C, Concheiro A, "Interactions of ibuprofen with cationic polysaccharides in aqueous dispersions and hydrogels rheological and diffusional implications", European Journal of Pharmaceutical Sciences 20 (4-5): 429-438, 2003, Rodriguez R, Alvarez-Lorenzo C, Concheiro A, "Influence of cationic cellulose structure on its interactions with sodium dodecylsulfate: implications on the properties of the aqueous dispersions and hydrogels", European Journal of Pharmaceutics and Biopharmaceutics 56 (1): 133-142 2003, Barreiro-Iglesias R, Alvarez-Lorenzo C, Concheiro A, "Thermal and FTIR characterization of films obtained from carbopol/surfactant aqueous solutions", Journal of Thermal Analysis and Calorimetry, 68 (2): 479-488 2002, Barreiro-Iglesias R, Alvarez-Lorenzo C, Concheiro A, "Incorporation of small quantities of surfactants as a way to improve the rheological and diffusional behavior of carbopol gels", Journal of Controlled Release, 77 (1-2): 59-75, 2001, Paulsson M, Edsman K, "Controlled drug release from gels using lipophilic interactions of charged substances with surfactants and polymers", Journal of Colloid and Interface Science, 248 (1): 194-200, 2002, Paulsson M, Edsman K, "Controlled drug release from gels using surfactant aggregates. II. Vesicles formed from mixtures of amphiphilic drugs and oppositely charged surfactants", Pharmaceutical Research, 18 (11): 1586-1592, 2001, Paulsson M, Edsman K, "Controlled drug release from gels using surfactant aggregates: 1. Effect of lipophilic interactions for a series of uncharged substances", Journal of Pharmaceutical Sciences, 90 (9): 1216-1225, 2001, Yan H, Tsujii K, Potential application of poly(N-isopropylacrylamide) gel containing polymeric micelles to drug delivery systems, Colloids and Surfaces B-Biointerfaces, 46 (3): 142-146, 2005].

It is an object of the present invention to provide a novel bioactive agent delivery system, particularly adapted for delivering the agent to the eye.

SUMMARY OF THE INVENTION

One embodiment of the invention relates to a bioactive agent delivery system comprising a substantially optically transparent contact lens having dispersed therein (1) at least one ophthalmically bioactive agent, said agent being capable of diffusion through said contact lens and into the post-lens tear film when said contact lens is placed on the eye and (2) associated with said bioactive agent, at least one ophthalmically compatible surfactant, said surfactant being present in an amount sufficient to attenuate the rate of migration of said bioactive agent through said contact lens.

A second embodiment of the invention is a method of administering a bioactive agent to a patient in need thereof comprising placing on the eye the above described drug delivery system.

Third and fourth embodiments of the invention concern a kit and its use for the storage and delivery of ophthalmic drugs to the eye, the kit comprising:

a) a first component containing at least one of the above described drug delivery systems, and b) a second component containing at least one storage container for the first component, the storage container additionally containing a material that substantially prevents the diffusion and migration of the ophthalmic drug during storage.

A fifth embodiment of the invention relates to a method of manufacturing a bioactive agent delivery system of claim 1 comprising providing a monomer mixture comprising a lens-forming monomer, the surfactant and the bioactive agent and polymerizing said monomer mixture.

Sixth and seventh embodiments of the invention concern articles of manufacture comprising packaging material and the above described drug delivery system or the above-described kit contained within the packaging material, wherein the packaging material comprises a label which indicates that the drug delivery system and kit can be used for ameliorating symptoms associated with pathologic conditions of the eye.

DETAILED DESCRIPTION OF THE INVENTION

The present invention is predicated on the discovery that contact lenses, preferably, sift contact lenses can function as new vehicles for ophthalmic drug delivery to reduce drug loss, eliminate systemic side effects, and improve drug efficacy.

The crux of the invention resides in the discovery that the rate of migration of bioactive agents, capable of diffusion through contact lenses and into the post-lens tear film when the contact lens is placed on the eye, is attenuated when the bioactive agent is associated with at least one ophthalmically compatible surfactant.

The contact lenses of the present invention are formed from reaction mixtures which comprise the reactive components, catalyst, other desired components, and optionally a solvent. The reaction mixtures may be cured using conventionally known conditions well known to those skilled in the art.

Hydrophilic components are those which when mixed, at 25° C. in a 1:1 ratio by volume with neutral, buffered water (pH about 7.0) form a homogenous solution. Any of the hydrophilic monomers known to be useful to make hydrogels may be used.

Exemplary of suitable hydrophilic monomers are DMA, HEMA, glycerol methacrylate, 2-hydroxyethyl methacrylamide, NVP, N-vinyl-N-methyl acrylamide, N-methyl-N-vinylacetamide, polyethyleneglycol monomethacrylate, methacrylic acid and acrylic acid, polymers or copolymers of any of the foregoing, mixtures thereof and the like.

The reaction mixtures may also comprise at least one hydrophobic component. Hydrophobic components are those which when mixed, at 25° C. in a 1:1 ratio by volume with neutral, buffered water (pH about 7.0) form an immiscible mixture.

Examples of suitable hydrophobic components include silicone containing components, fluorine containing components, components comprising aliphatic hydrocarbon groups having at least 3 carbons, mixtures thereof and the like.

The term component includes monomers, macromers and prepolymers. "Monomers" refers to lower molecular weight compounds that can be polymerized to higher molecular weight compounds, polymers, macromers, or prepolymers. The term "macromer" as used herein refers to a high molecular weight polymerizable compound. Prepolymers are partially polymerized monomers or monomers which are capable of further polymerization.

The invention is exemplified herein using soft hydrogel lenses that are made of poly 2-hydroxyethyl methacrylate p-(HEMA). However, it will be understood by those skilled in the art that the range of materials that may be employed as vehicles in the present invention is limited only by the selection of materials that may be employed in the manufacture of contact lenses and the nature of the particular ophthalmic drug to be incorporated therein. The term, "optically transparent" as used herein is intended to refer to a degree of transparency equivalent to that of p-HEMA or other material employed as a contact lens. The p-HEMA hydrogel matrix may be synthesized by any convenient method, e.g., bulk or solution free radical polymerization of HEMA monomers in presence of a cross linker such as ethylene glycol-di-methacrylate (EGDMA) [Mandell, R. B., "*Contact Lens Practice: Hard and Flexible Lenses*", 2nd ed., Charles C. Thomas, Springfield, vol. 3, 1974].

Addition of the bioactive agent and surfactant to the polymerizing medium followed by polymerization could result in the formation of self assembled surfactant aggreagtes that contain the bioactive agent. If contact lenses made of this material are placed on the eye, the drug molecules will diffuse from the surfactant aggregates, travel through the lens matrix, and enter the post-lens tear film (POLTF), i.e., the thin tear film trapped in between the cornea and the lens. In the presence of the lens, drug molecules will have a much longer residence time in the post-lens tear film, compared to about 2-5 minutes in the case of topical application as drops [Bourlais, C. L., Acar, L., Zia H., Sado, P. A., Needham, T., Leverge, R., "*Ophthalmic drug delivery systems*". Progress in retinal and eye research, 1998, 17, 1: 33-58; Creech, J. L., Chauhan, A., Radke, C. J., "*Dispersive mixing in the posterior tear film under a soft contact lens*", I&EC Research, 2001, 40: 3015-3026; McNamara, N. A., Polse, K. A., Brand, R. D., Graham, A. D., Chan, J. S., McKenney, C. D., "*Tear mixing Under a soft contact lens: Effects of lens diameter*". Am. J. of Ophth., 1999, 127(6): 659-65]. The longer residence time will result in a higher drug flux through the cornea and reduce the drug inflow into the nasolacrimal sac, thus reducing drug absorption into the blood stream. In addition, due to the slow diffusion of the drug molecules through the particles, drug-laden contact lenses can provide continuous drug release for extended periods of time.

Without wishing to be bound by any theory, the inventors believe that the mechanism of attenuation of migration of the active agent is one of entrapment of the agent in a miscelle or inverse micelle structure formed by the surfactant.

Suitable surfactants include any ophthalmically compatible surfactants capable of providing the necessary attenuation in release rates without affecting the optical transparency of the resulting contact lens. The examples presented here utilize nonionic surfactants but it should be understood that cationic, anionic, and zwitterionic surfactants are equally applicable. Also both linear and branched surfactants may be utilized. Exemplary of suitable surfactants are the following.

Block copolymers, which are surface active, are classified by the ratio of the hydrophilic and lipophilic segments in the molecule. A large number of commercial emulsifying agents, such as surfactants, have been assigned a hydrophilic/lipophilic balance (HLB) number. The block copolymer consists of a hydrophilic moiety (water soluble) and a hydrophobic moiety.

The preferred water soluble (hydrophilic) region of the block copolymer consists of polyethylene glycol, polyethylene oxide, polyvinyl alcohol, polyacrylamide, polymethacrylamide, poly(vinylpyrrolidone), and the like. It is most preferred that the hydrophilic moiety is polyethylene glycol, polyacrylamide, polymethacrylamide, poly (vinylpyrrolidone) or polyvinyl alcohol. The most preferred hydrophilic core is polyethylene glycol.

The hydrophobic polymer segment is attached to the hydrophilic polymer by non-hydrolyzable chemical bonds, such as carbon-carbon bonds, by amide linkage, ether linkages, ester linkages, thio linkages, amino linkages, and the like. The preferred hydrophobic polymer segments include linear and branched carbon chains (both saturated and unsaturated), poly propylene oxide, poly hydroxy butyrate, polystyrene, etc. The preferred hydrophobic polymer segments also include poly(α-hydroxycarboxylic acids) which are derived from either glycolide or lactide; poly(ω-hydroxycarboxylic acids) which are derived from either ω-lactone or δ-lactone or ε-lactone; or those derived from a copolymer of such include poly(α-hydroxycarboxylic acids) with such poly(ω-hydroxycarboxylic acids). The hydrophobic polymer segments may have an ethylenically unsaturated polymerizable group at one end which is opposite to the one at which the hydrophobic polymer segment is bonded to the hydrophilic polymer segment. Such a polymerizable group can be introduced from (meth)acrylic acid or vinylbenzyl chloride. Furthermore, such a polymerizable group may be subjected to a polymerization reaction after the formation of the polymer, and is thus brought into a polymerized (crosslinked) state. In such a state, the polymer per se is more stable.

The most preferred polymer is formed from a block copolymer which is composed of both a hydrophilic polymer segment essentially comprising poly (ethyleneglycol) [hereinafter sometimes abbreviated as PEG] and a hydrophobic polymer segment. The phrase "essentially comprising" means that PEG occupies the main portion of the hydrophilic polymer segment, and that some linking group or the like which has essentially no influence on the hydrophilicity of said segment may be contained in some amount in the PEG chain or between hydrophilic and hydrophobic polymer segments. However, it is preferable that the PEG chain consists of PEG alone.

Examples of block copolymers are found in U.S. Pat. No. 5,925,720, to Kataoka, et al., U.S. Pat. No. 5,412,072 to Sakarai, et al., U.S. Pat. No. 5,410,016 to Kataoka, et al., U.S. Pat. No. 5,929,177 to Kataoka, et al., U.S. Pat. No. 5,693,751 to Sakurai, et al., U.S. Pat. No. 5,449,513 to Yokoyama, et al., WO 96/32434 and WO 96/33233, the contents of all of which are incorporated by reference. Modifications thereof which are prepared by introducing thereon a suitable functional group (including an ethylenically unsaturated polymerizable group) are also examples of block copolymers from which surfactants of the present invention are preferably prepared.

The contact lens may be formed by the polymerization of any suitable reactive components or mixtures of reactive components known in the art to produce contact lenses an, in which the bioactive agent may be microemulsified by the surfactant and in which the bioactive agent migrates when placed on the eye. The lens material may be hydrophillic or hydrophobic.

The lens-forming or reactive components include monomers, prepolymers and macromers that are polymerizable by free radical polymerization, generally including an activated unsaturated radical, and most preferably an ethylenically unsaturated radical.

Additional additives, which are generally known in the art may also be included. Additives include but are not limited to wetting agents, ultra-violet absorbing compounds, tints, pigments, photochromic compounds, release agents, combinations thereof and the like. The additional compounds may be reactive or non-reactive.

An especially preferred class of materials are hydrogel copolymers. A hydrogel is a crosslinked polymeric system that can absorb and retain water in an equilibrium state. Accordingly, for hydrogels, the monomer mixture will typically include at least one hydrophilic monomer and a crosslinking agent (a crosslinker being defined as a monomer having multiple polymerizable functionalities). Suitable hydrophilic monomer include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone; and acrylamides, such as methacrylamide and N,N-dimethylacrylamide. Typical crosslinking agents include polyvinyl, typically di- or tri-vinyl monomers, such as di- or tri(meth)acrylates of diethyleneglycol, triethyleneglycol, butyleneglycol and hexane-1,6-diol; divinylbenzene; and others known in the art.

Another class of lens-forming monomers are those that form silicone hydrogel copolymers. Such systems include, in addition to a hydrophilic monomer, a silicone-containing monomer. Such bulky monomers specifically include methacryloxypropyl tris(trimethylsiloxy)silane, pentamethyldisiloxanyl methylmethacrylate, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate, monomethacryloxypropyl terminated mono-n-butyl terminated polydimethylsiloxane, mono-(3-methacryloxy-2-hydroxypropyloxy)propyl terminated, mono-butyl terminated polydimethylsiloxane, bis-3-methacryloxy-2-hydroxypropyloxypropyl polydimethylsiloxanes, 3-methacryloxy-2-hydroxypropyloxy)propylbis (trimethylsiloxy)methylsilane, combinations thereof and the like.

Another suitable class are multifunctional ethylenically "end-capped" siloxane-containing monomers, especially difunctional monomers. Other silicone-containing monomers include the silicone-containing monomers described in U.S. Pat. Nos. 5,034,461, 5,610,252 and 5,496,871, the disclosures of which are incorporated herein by reference. Many other silicone-containing monomers are well-known in the art.

The invention is illustrated by the following non-limiting examples wherein the formulations are based on adding surfactants to polymerizing mixtures. The surfactants explored here are linear ethoxylated surfactants (commonly referred as Brij) containing the same alkyl chain length (CIS) and increasing numbers of ethoxylate (EO) units (10, 02 and 100). Here, are reported formulations and fabrication processes for surfactant-laden HEMA based soft contact lenses, and several examples for the loading of ophthalmic drugs such as cyclosporine, and the release of the drugs under conditions that simulate ocular conditions. The results show that the Brij surfactants are very effective at providing extended release of cyclosporine for a period of about 20-25 days. Amongst the three types of Brij surfactants explored, Brij 78 provides the best release behavior. The surfactant-laden gels were subjected to the same processing conditions as contact lenses such as extraction, autoclaving, storage, and these steps did not impact the release rates from the gels. Thus, Brij surfactant laden gels are excellent candidates for the delivery of cyclosporine. These systems may also be adapted to deliver other ophthalmic drugs.

EXAMPLES

Example 1

Synthesis of Gels Containing Brij 97

To prepare Brij 97 laden gels with 1.5% surfactant loading in dry state, 0.2 g of surfactant was dissolved in 10 ml of Dl water, and then stirred at about 600 rpm at room temperature till the surfactant completely dissolved in the water phase. Separately, 3.5 mg of CyA was dissolved in 2.7 ml of HEMA monomer and stirred at 600 rpm for a period of 5 hours. Next, 15 ml of the crosslinker (EGDMA) and 2 ml of surfactant solution were added to the drug containing HEMA solution. The solution was then degassed by bubbling nitrogen for 10 minutes. Next, 6 mg of the initiator (TPO) was added and the solution was stirred at 300 rpm for 10 minutes to ensure complete dissolution of the initiator. The mixture was then poured in between two glass plates that were separated from each other by 200 (for thick gels) or 100 mm (for thin gels) thick sheet. The polymerization reaction was performed under UV light for 40 minutes. To prepare gels with higher surfactant loading, the amount of surfactant added to the 10 ml DI water was increased. Specifically, 0.2, 0.6, 1.5 g of Brij 97 was added to fabricate gels with 1.5%, 3.5%, 8% surfactant loading in dry gel, respectively. To synthesize HEMA gels without surfactants, 2 ml of the surfactant solution was replaced by 2 ml DI water, and the drug was directly added to the mixture of HEMA, EGDMA and DI water. To synthesize HEMA gels loaded with other surfactants, the same procedure as described above was followed except that Brij 97 was replaced by an equal amount of the desired surfactant.

Example 2

Drug Release Studies

Figure 1:
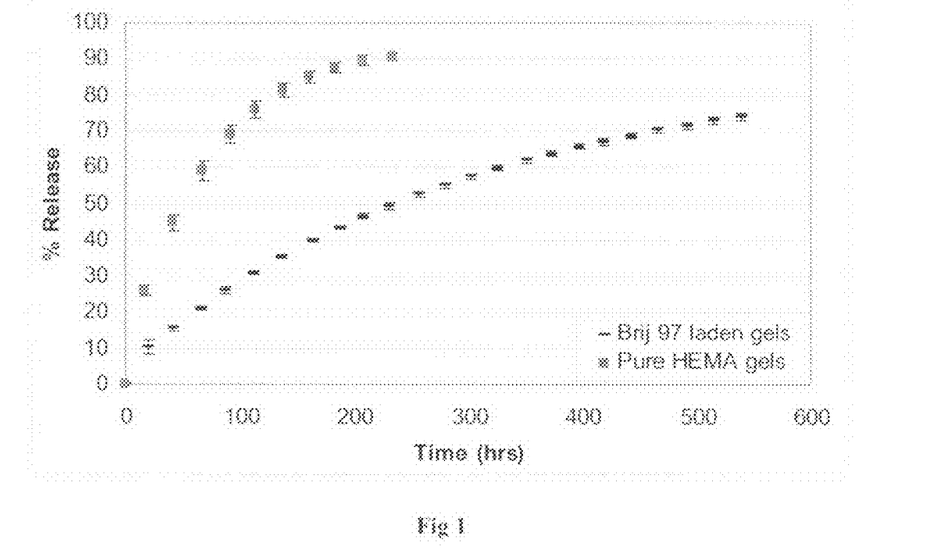
FIGS. 1-7 depict drug release rates in several embodiments of the invention.

The gels prepared by the procedure described above were cut into pieces that were about 40 mg in weight. In some cases these gels were soaked in a large volume of volume/PBS to extract the unreacted monomer. This step is referred to as the initial extraction. The drug release studies reported below were conducted with a 40 mg gel which was soaked in 3.5 ml PBS and the PBS was replaced every 24 hours. An extraction step was not performed in these experiments. For comparison, pure HEMA gels were loaded with the same amount of drug as the surfactant laden gels, and drug release studies was also performed from these gels. The release of cyclosporine from pure HEMA gels and that from the Brij 97 laden gels with 8% surfactant loading (based on weight of surfactant in dry gel) is shown in FIG. 1 [Comparison of release from Brij 97 surfactant laden gels and HEMA gels. The gels were 200 mm thick in dry state and the amount of drug in the gels was 50 mg. Data is represented as mean std (n=3)].

The cyclosporin release from HEMA gels last only about 6-7 days but the surfactant-laden gels release drug for about 25 days. This clearly demonstrates a significant reduction in delivery rate and an increase in the duration of release on addition of surfactant to the gels. It is speculated that the surfactant molecules may be forming aggregates such as micelles, and since cyclosporine is a hydrophobic molecule, a larger fraction of the entrapped drug may be present in the hydrophobic domains of the surfactant aggregates. Thus, the drug concentration in the aqueous phase in the gel may be much smaller for the surfactant containing gels compared to the pure HEMA gels, and the lower free drug concentration may be causing the slower release. Additionally, the drug may face a barrier to diffuse out from the hydrophobic domains, and this may cause an additional reduction in the drug release rates.

Example 3

Dependence of the Release Rates on the Surfactant Loading

As stated above, the results shown in FIG. 1 are for a system that had 8% surfactant loading in the dry gel. To investigate the effect of the surfactant loading on the drug release rates, it was decided to prepare gels with two different surfactant loadings. Table 1 shows the dry gel weight percentages of surfactant and cyclosporine for the two gels with different surfactant loadings.

Table 1 Composition of gels that were used to study the effect of surfactant loading on drug release profiles from Brij 97 laden gels Drug release experiments were performed on these two gels with protocols described above, and the results are compared below in FIG. 2 [Effect of surfactant concentration on drug release profiles from Brij 97 laden gels. The compositions of the gels are reported in Table 1. The gels were 200 mm thick in dry state and the amount of drug in the gels was 48 mg].

Figure 2:
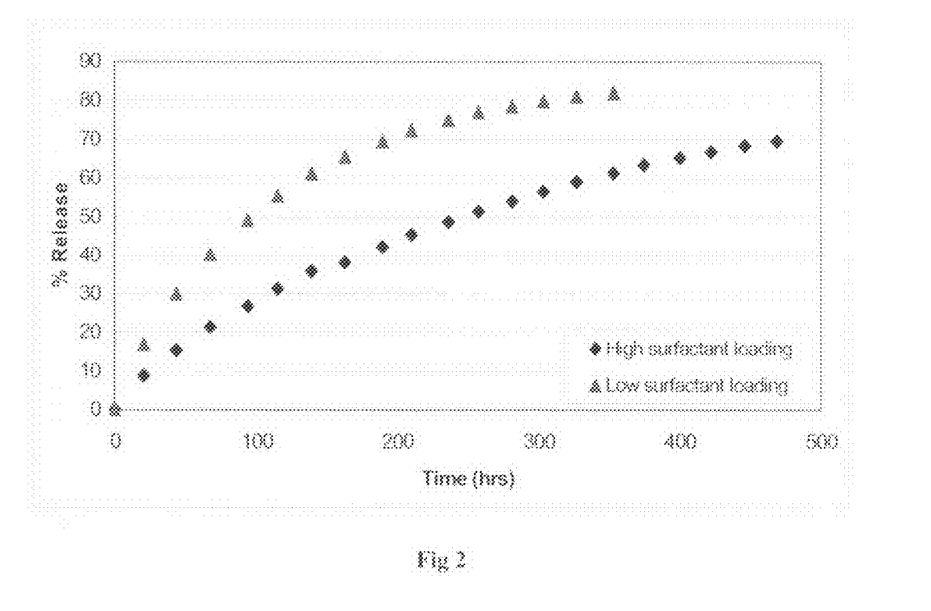

As shown in the figure, the release rates depend strongly on the surfactant loading. The gel with 8.4% surfactant loading releases CyA for about 500 hours but the gel with 1.4% surfactant loading releases the drug for about 300 hours, which is only marginally longer than the duration of release for HEMA gels. The reductions in release rates due to an increase in surfactant concentration may be attributed to an increase in the number and/or size of surfactant aggregates that may be forming in the gel.

Example 4

Effect of Gel Thickness on Drug Release Profiles

Figure 3:
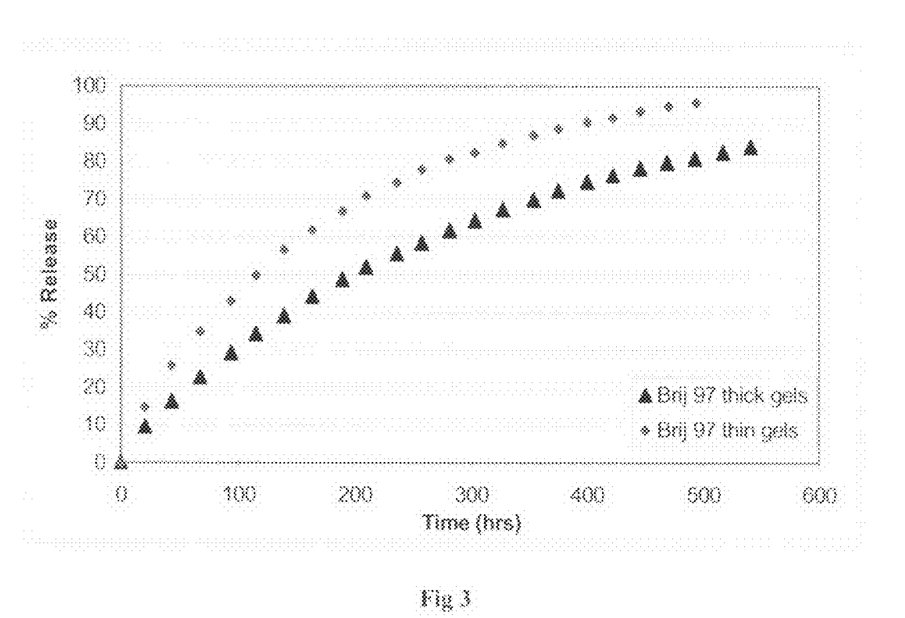

The results presented above were obtained with 200 μm thick gels. Typical contact lenses are about 100 μm thick, and so it was decided to explore the effect of gel thickness on release profiles. To explore this issue, two different sets of drug containing surfactant-laden gels were synthesized. One set of these gels were about 200 μm thick and the others were about 100 μm thick. The surfactant loading for both of these gels was 8% w/w for dry gel. The drug was loaded into the gels by directly dissolving it into the HEMA monomer. It is noted that the weights of both the thick and then thin gels were about same because the cross sectional area of the thin gel was double that of the thick gel. As shown in FIG. 3 [Effect of thickness on drug release profiles for Brij-97 laden gels. The thick and the thin gels were 200 mm and 100 mm thick in dry state, respectively, and the amount of drug in the gels was 47 mg. These gels had 8% surfactant (w/dry gel w)], the release rates are slightly slower for the thick gels, but the effect is minor. If the drug release profiles were controlled by diffusion, a change in thickness by a factor of 2 would lead to a significant reduction in release time. Since we clearly do not observe a significant reduction in the release duration, it can be concluded that the drug release process is not controlled by diffusion through the gel but by other processes such as transport from the hydrophobic regions of the surfactant aggregates.

Example 4

Effect of Gel Thickness on Drug Release Profiles

The results presented above were obtained with 200 μm thick gels. Typical contact lenses are about 100 μm thick, and so it was decided to explore the effect of gel thickness on release profiles. To explore this issue, two different sets of drug containing surfactant-laden gels were synthesized. One set of these gels were about 200 μm thick and the others were about 100 μm thick. The surfactant loading for both of these gels was 8% w/w for dry gel. The drug was loaded into the gels by directly dissolving it into the HEMA monomer. It is noted that the weights of both the thick and then thin gels were about same because the cross sectional area of the thin gel was double that of the thick gel. As shown in FIG. 3 [Effect of thickness on drug release profiles for Brij-97 laden gels. The thick and the thin gels were 200 mm and 100 mm thick in dry state, respectively, and the amount of drug in the gels was 47 mg. These gels had 8% surfactant (w/dry gel w)], the thin gels release drug at a more rapid rate than the thick gels but the duration of release for the thin gels is still about 500 hours.

Example 5

Effect of processing conditions on drug release: In order to evaluate the suitability of the Brij 97 surfactant-laden gels as contact lenses, it was decided to fabricate gels with the same thickness as contact lenses, and take these gels through processing conditions very similar to those used for typical contact lenses. The results of these studies are shown below.

(1) Synthesis: The synthesis procedures were identical to those described earlier for preparing Brij 97-laden gels. Gels were prepared with three different surfactant loadings (1.5, 3.5 and 8.3%). All the gels used in these studies were about 100 μm thick and did not contain any drug. The drug was loaded later by soaking the gels in aqueous drug solutions.

(2) Extraction: The unreacted monomer was extracted from the gels by soaking gels that weighed about 40 mg in 10 ml of water at 50° C. The Dl water was replacing every 5 minutes for 5 times. So the total duration for the extraction step was 25 minutes.

(3) Drug Loading: After extraction, each gel was soaked in 4 ml of cyclosporine solution in DI water at a concentration of 12 μg/ml for a period of 12 days. At the end of the loading phase, the concentration in the solution was measured. The drug uptake by the gel was then determined by calculating the difference between the initial and the final drug amounts in the solution.

The results for the drug loaded into two sets of controls (pure HEMA gels) and two sets of 1.5%, 3.5% and 8% surfactant containing gels are shown in Table 2.

TABLE 2

Drug uptake by Brij 97-laden gels during soaking

| Sample | Drug in solution initially (mg) | Drug remaining in the solution after 12 days (mg) | Amount of drug inside the gel system (mg) |
|---|---|---|---|
| PureHEMA1 | 48 | 31.8 | 16.2 |
| PureHEMA2 | 48 | 27.1 | 20.9 |
| 8% surfactant1 | 48 | 17.4 | 30.6 |
| 8% surfactant2 | 48 | 19 | 29 |
| 3.5% surfactant1 | 48 | 22.9 | 25.1 |
| 3.5% surfactant2 | 48 | 27.1 | 20.9 |
| 1.5% surfactant1 | 48 | 23.6 | 24.4 |
| 1.5% surfactant2 | 48 | 22.7 | 25.3 |

(4) Autoclaving: After drug loading, each gel was soaked in 1.5 ml of Dl water and autoclaved for 15 min at 121° C.

(5) Shelf storage: After autoclaving, the samples were stored at room temperature for a period of 10 days. After the 10 day period, the concentration in the aqueous phase was measured to determine the amount of drug that was released from the gel during the autoclaving and shelf storage. By subtracting this amount from the amount of drug taken up by the gel, the remaining amount of drug left in the gel was determined. The result for the drug retained by the gels after the storage are shown in Table 3.

TABLE 3

Table 3: Summary of drug release studies from Brij 97-laden gels

| | Amount of drug inside the gel system before autoclaving (mg) | Amount of drug released during shelf storage (mg) | Amount of drug remaining inside the gel (mg) | Amount of drug released during drug release experiments (mg) |
|---|---|---|---|---|
| PureHEMA1 | 16.2 | 6.2 | 10 | 6.8 |
| PureHEMA2 | 20.9 | 6.2 | 14.7 | 5.6 |
| 8% surfactant1 | 30.6 | 5.2 | 25.4 | 22.1 |
| 8% surfactant2 | 29 | 5.7 | 23.3 | 22.1 |
| 3.5% surfactant1 | 25.1 | 4.5 | 20.6 | 19.2 |
| 3.5% surfactant2 | 20.9 | 4.4 | 16.5 | 20.8 |
| 1.5% surfactant1 | 24.4 | 6.9 | 17.5 | 13.9 |
| 1.5% surfactant2 | 25.3 | 7 | 18.3 | 15.3 |

Figure 4:
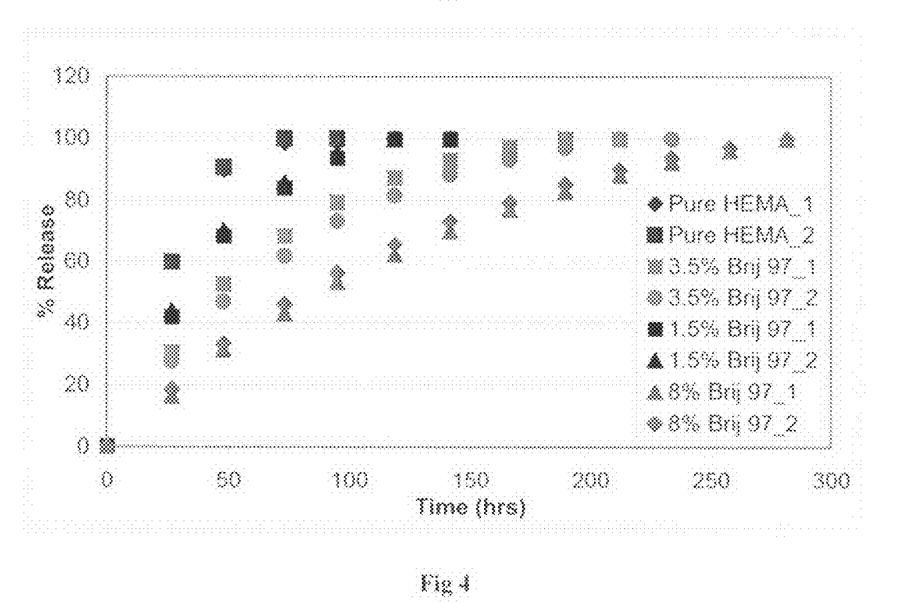

(6) Drug release: In the final step, each gel was submerged in 3.5 ml of PBS, which was replaced every 24 hours, and the concentration of the drug was measured by HPLC. The elution time of cyclosporine that diffused out of the gels after autoclaving was compared with the control to ensure that the drug did not degrade during the processing steps. The drug release profiles for the cumulative % release as a function of time are plotted in FIG. 4 [Effect of the surfactant loading on drug release profiles for Brij 97 surfactants laden gels. All the gels were about 100 mm in thickness. The amount of drug in each gel and the total cumulative release are noted in Table 3].

Also, total cumulative release from the gels is listed in the last column in Table 3. A comparison of the total cumulative release (5th column in Table 3) with the amount of drug retained by the gel (4th column in Table 3) shows that almost the entire amount of the drug retained by the surfactant-laden gels diffuses out during the drug release experiments. However, for pure HEMA gels there is a significant difference between these values. We believe that the discrepancy may be due to an overestimation of the drug loaded into the gel because of neglect of drug absorption on the surface of the glass vials. This underestimation is more important for HEMA gels because the bulk drug concentration is higher for HEMA gels and so there is a larger adsorption on the glass surface.

Example 6

Effect of Hydrophilic Chain Length

To understand the mechanisms involved in transport of drug in the surfactant laden gels, it was decided to fabricate gels with three Brij surfactants with the same hydrophobic group but different lengths of the hydrophilic (EO) group. Table 4 lists the properties of the surfactants that were considered in this study.

Figure 5:
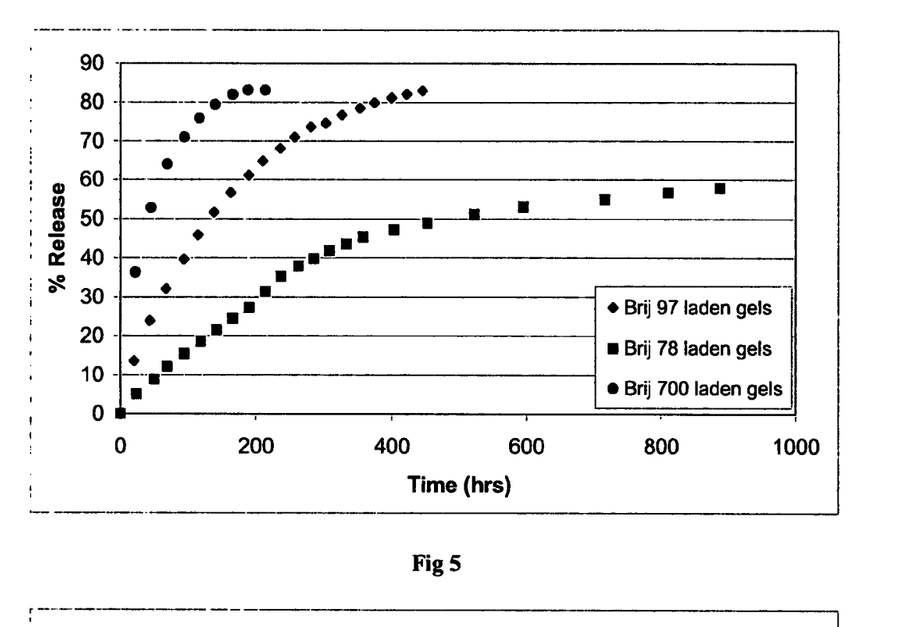

The procedures for preparing these gels and performing the drug release experiments are the same as those detailed above. It is noted that drug was loaded into the gels by dissolving it in the HEMA phase and that the initial monomer extraction was not conducted for these gels. The drug release profiles for 100 μm thick gels with 8% surfactant loading are shown in FIG. 5 [Effect of the length of the hydrophilic group (EO) on drug release profiles for Brij surfactant laden gels. All the gels were about 100 mm in thickness and the amount of drug in the gels was 48 mg] for the three types of surfactants. Results show that the drug release from Brij 700 gels (100 EO units) is similar to that from pure HEMA gels. This may be expected because the fraction of hydrophobic segment is very small for Brij 700 and so there are almost negligible hydrophobic regions in Brij 700 gels. Interestingly, even though Brij 78 (20 EO units) has less hydrophobic fraction compared to Brij 97 (10 EO units), Brij 78-laden gels release drug at a much slower rate than the Brij 97 gels. This behavior may be due to the fact that even though Brij 78 gels have less volume of hydrophobic regions such as cores of micelles, the longer EO chains offer a higher barrier for transport of the drug from the hydrophobic regions to the bulk.

Example 7

Effect of Brij 78 Loading on Release Behavior

Figure 6:
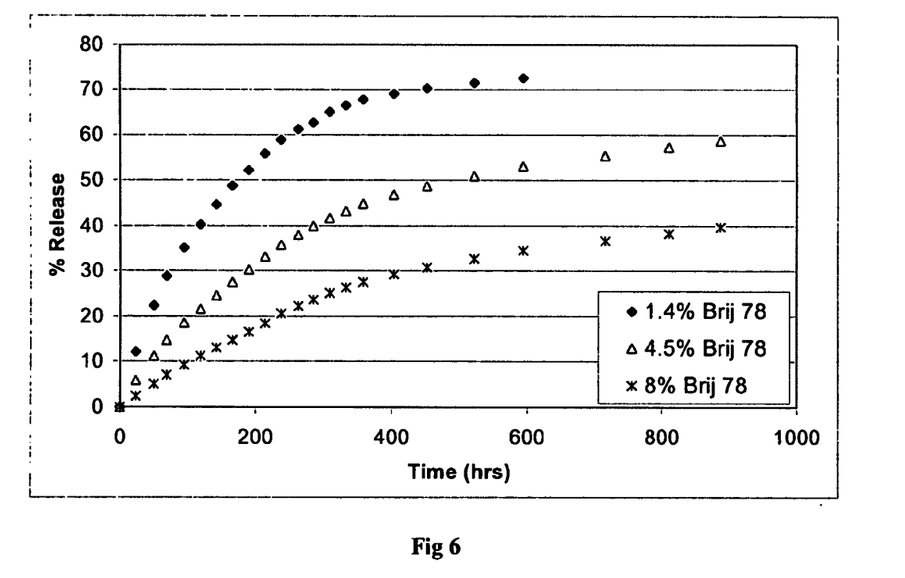

Since Brij 78 systems seem to be more suitable than Brij 97 systems for extended delivery of cyclosporine; it was decided to explore the dependency of release rates on the surfactant loading for Brij 78 laden gels. Three different surfactant concentrations (1.4%, 4.5% and 8% w/dry gel w) were explored and the release profiles are shown in FIG. 6 [Effect of the surfactant loading on drug release profiles for Brij 78 surfactant laden gels. All the gels were about 200 mm in thickness and the amount of drug in the gels was 50 mg]. The gels utilized in these studies were 200 µm thick. The results in FIG. 6 show that an increase in the surfactant concentration has a significant effect on the drug release rates. Importantly, even with 1.4% surfactant loading, these systems release drug for about 400 hours, and if the loading is increased to 4.5%, the release duration increases to more than 900 hours.

Example 8

Effect of Thickness on Drug Release from Brij 78 Laden Gels

Figure 7:
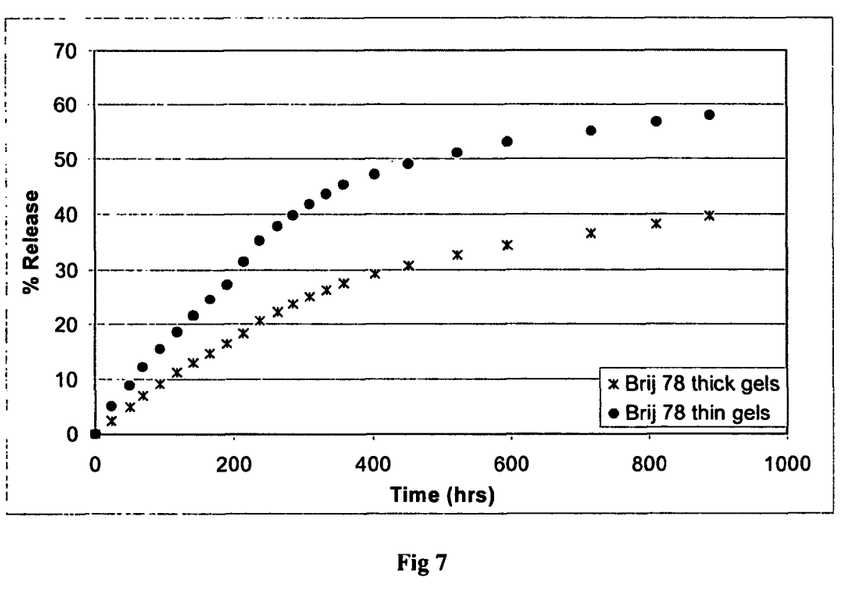

The results presented above were obtained with 200 µm thick gels. We further decided to explore the effect of gel thickness on release profiles for Brij 78 laden gels. The drug was loaded into the gels by dissolving it in the HEMA solution before polymerization. Drug release profiles for 100 µm thick and 200 µm thick Brij 78 laden gels are compared in FIG. 7 [Effect of thickness on drug release profiles for Brij-78 laden gels. The thick and the thin gels were 200 mm and 100 mm thick in dry state, respectively, and the amount of drug in the gels was 48 mg. These gels had 8% surfactant (w/dry gel w)].

Brij surfactant laden systems for ophthalmic drug delivery by contact lenses have been demonstrated. HEMA gels loaded with three different types of Brij surfactants were synthesized. These surfactants have the same hydrophobic segment but different lengths of hydrophilic (EO) segment. Cyclosporine was loaded into these systems by dissolving it in HEMA before polymerization, and in some cases, by soaking the surfactant-laden gels in aqueous cyclosporine solutions. Experiments were conducted to study the effects of surfactant type, concentration and gel thickness on release profiles. Furthermore, for Brij 97 systems, experiments were performed to simulate the various processes in contact lens manufacturing such as extraction, autoclaving and storage. Results from all these studies show that the Brij 97-laden gels release cyclosporine in PBS for a period of about 20-25 days. The release duration depends weakly on thickness, but strongly on surfactant concentration. These systems are very promising and can be used for extended release of cyclosporine from contact lenses. Brij 78 systems are even more promising because these systems release cyclosporine for longer periods of time compared to Brij 97 systems. In fact with only 4.5% surfactant loading, Brij 78 loaded gels release cyclosporine for about 900 hours. Brij 78 surfactants have other advantages over the Brij 97 surfactants such as a longer chain length, which is expected to reduce the flux of the surfactant from the gel into the eye. Furthermore, Brij 78 surfactants have been used in ocular studies as cornea permeability enhancers, and so these are not expected to cause any toxic response in the eyes. While the examples reported here were conducted with cyclosporine, other drugs could also be dissolved in the HEMA, but the release rates may not be as slow as those for cyclosporine, particularly if the drug molecules are much smaller than cyclosporine. It will be appreciated by those skilled in the art that these systems can be made suitable for other drugs by using mixed surfactants that will pack more tightly. It is also noted that in addition to surfactants, other self assembling molecules such as lipids, and block-co-polymers could be used to create domains that could trap and slowly release hydrophobic drugs. It is further noted that similar ideas could be used to create hydrophilic domains in silicone contact lenses which are hydrophobic in nature. Hydrophilic drugs can then be trapped and slowly released from these hydrophilic domains in the silicone contact lenses.

The invention claimed is:

1. A bioactive agent delivery system comprising a contact lens having dispersed therein (1) an ophthalmically bioactive agent, said agent being capable of diffusion through said contact lens and into the post-lens tear film when said contact lens is placed on the eye and (2) associated with said bioactive agent, at least one ophthalmically compatible polymeric surfactant, said surfactant being present in an amount sufficient to form aggregates or micelles and attenuate the rate of migration of said bioactive agent through said contact lens.

2. A bioactive agent delivery system of claim 1 wherein said polymeric surfactant comprises a block copolymer having a hydrophobic segment and a hydrophilic segment.

3. A bioactive agent delivery system of claim 2 wherein said bioactive agent is hydrophobic and is associated with the hydrophobic segment of said surfactant.

4. A bioactive agent delivery system of claim 1 wherein said contact lens comprises a polymer formed from a reaction mixture comprising at least one hydrophilic monomer.

5. A bioactive agent delivery system of claim 4 wherein said hydrophilic monomer is an unsaturated carboxylic acid; acrylic substituted alcohol; vinyl lactam or acrylamide.

6. A bioactive agent delivery system of claim 5 wherein said hydrophilic monomer is selected from the group consisting of methacrylic or acrylic acid, 2-hydroxyethyl methacrylate, 2-hydroxyethylacrylate, N-vinyl pyrrolidone, methacrylamide, N-vinyl-N-methacetamide, N,N-dimethylacrylamide, and mixtures thereof.

7. A bioactive agent delivery system of claim 1 wherein said bioactive agent is hydrophilic and is associated with the hydrophilic segment of said surfactant.

8. A bioactive agent delivery system of claim 1 wherein said contact lens comprises a hydrophobic material.

9. A bioactive agent delivery system of claim 8 wherein said hydrophobic material is selected from the group consisting of a silicone, silicone containing prepolymers and macromers, polydimethylsiloxane, pentamethyldisiloxanyl methylmethacrylate, tris(trimethylsiloxy)methacryloxy propylsilane, methyldi(trimethylsiloxy)methacryloxymethyl silane, monomethacryloxypropyl terminated mono-n-butyl terminated polydimethylsiloxane, mono-(3-methacryloxy-2-hydroxypropyloxy)propyl terminated, mono-butyl terminated polydimethylsiloxane, bis-3-methacryloxy-2-hydroxypropyloxypropyl polydimethylsiloxanes, 3-methacryloxy-2-hydroxypropyloxy)propylbis(trimethylsiloxy) methylsilane, 3-[tris(trimethylsiloxy)silyl]propyl vinyl carbamate, methyl methacrylate, ethylene glycol dimethacrylate, and mixtures thereof.

10. The bioactive agent delivery system of claim 1 wherein said polymeric surfactant is present at such a level to provide at least 1.5% surfactant loading in a dry gel.

11. The bioactive agent delivery system of claim 1 wherein said polymeric surfactant is present at such a level to provide at least 3.5% surfactant loading in a dry gel.

12. The bioactive agent delivery system of claim 1 wherein said polymeric surfactant is present at such a level to provide at least 8.0% surfactant loading in a dry gel.

13. The bioactive agent delivery system of claim 1 wherein said contact lens has a drug loaded within and said polymeric surfactant operates to extend the release of the drug over a period of about 25 days.

14. The bioactive agent delivery system of claim 1 wherein said polymeric surfactant is present at such a level to provide about 1.4% surfactant loading in a dry gel and a drug release duration of about 400 hours.

15. The bioactive agent delivery system of claim 1 wherein said polymeric surfactant is present at such a level to provide at least 4.5% surfactant loading in a dry gel and a drug release duration of about 900 hours.

* * * * *

UNITED STATES PATENT AND TRADEMARK OFFICE
CERTIFICATE OF CORRECTION

| | | |
|---|---|---|
| PATENT NO. | : 8,075,909 B2 | Page 1 of 1 |
| APPLICATION NO. | : 11/896608 | |
| DATED | : December 13, 2011 | |
| INVENTOR(S) | : Chauhan et al. | |

It is certified that error appears in the above-identified patent and that said Letters Patent is hereby corrected as shown below:

Title Page 2 - Item (56) Column 2, lines 33-69, delete publications listed in duplicate.

Signed and Sealed this
Seventh Day of February, 2012

David J. Kappos
*Director of the United States Patent and Trademark Office*